(12) United States Patent
Ruiz-Roso Calvo De Mora et al.

(10) Patent No.: US 8,663,708 B2
(45) Date of Patent: Mar. 4, 2014

(54) PRODUCT OF VEGETAL ORIGIN COMPRISING PROANTHOCYANIDINES AND ITS PREPARATION PROCESS

(75) Inventors: Baltasar Ruiz-Roso Calvo De Mora, Majadahonda (ES); Ana Maria Requejo Marcos, Madrid (ES); Lourdes Perez-Olleros Conde, Madrid (ES); José Antonio Holguín Hueso, Madrid (ES)

(73) Assignees: Investigacion y Nutricion, S.L., Madrid (ES); Wild Valencia, S.A., Valencia (ES)

( * ) Notice: Subject to any disclaimer, the term of this patent is extended or adjusted under 35 U.S.C. 154(b) by 1144 days.

(21) Appl. No.: 11/571,237

(22) PCT Filed: Jun. 21, 2005

(86) PCT No.: PCT/EP2005/052877
§ 371 (c)(1),
(2), (4) Date: Dec. 22, 2006

(87) PCT Pub. No.: WO2006/000551
PCT Pub. Date: Jan. 5, 2006

(65) Prior Publication Data
US 2008/0063733 A1 Mar. 13, 2008

(30) Foreign Application Priority Data
Jun. 23, 2004 (ES) .................................. 200401626

(51) Int. Cl.
*A61K 36/00* (2006.01)
(52) U.S. Cl.
USPC ............................ 424/725; 424/776; 424/777
(58) Field of Classification Search
None
See application file for complete search history.

(56) References Cited

U.S. PATENT DOCUMENTS

| | | | | |
|---|---|---|---|---|
| 3,950,553 | A * | 4/1976 | Gasser et al. | 426/262 |
| 4,282,264 | A * | 8/1981 | Magnolato | 426/599 |
| 6,361,807 | B1 * | 3/2002 | Aviram et al. | 424/744 |
| 2003/0077374 | A1 * | 4/2003 | Ohishi et al. | 426/597 |

FOREIGN PATENT DOCUMENTS

| | | |
|---|---|---|
| EP | 0713706 | 5/1996 |
| WO | WO 90/13304 | 11/1990 |
| WO | WO 2004/014150 | 2/2004 |

OTHER PUBLICATIONS

Wursch P et al: "Tannin Granules from Ripe Carob Ceratonia-Siliqua Pod", Lebensrnittel-Wissenschaft and Technologie, vol. 17, No. 6, 1984, pp. 351-354, La Tour de Peilz, Switzerland.
Marakis S: "Carbo Bean in Food and Feed: Current Status and Future Potentials—a Critical Appraisal", Journal of Food Science and Technology, Association of Food Scientists and Technologists, US, vol. 33, No. 5, 1996, pp. 365-383, Athens, Greece.
European Patent Office, Examination Report for International Application No. 05 760 934.9, Jan. 31, 2008.
Response to the Examination Report for International Application No. 05 760 934.9, Feb. 18, 2008, with attachments Annex-1 and Annex-2.
Abu Bakr Mahammad Bin Zakariyya Al-Razi; Kitaab-al-Haawi-fil-Tibb, vol. XX (9th century AD), Dayerah-al-Ma'aarif Usmania, Hyderabad (First Edition) 1967 AD p. 516 Formulation ID: AAA20/5870 Formulation Name: Dawa Bara-e-Khafaqaan.
Agnivesa; Caraka Samhita—Edited and translated by P.V. Sharma, vol. II: Chaukamba Orientalia Varanasi Edn. 5th, 2000 [Time of origin 1000 BC—4th century] p. 340 Formulation ID: BP/2643C Formulation Name: Apatantrakaharahinguvadiyogah.
Mahendra Bhaugika; Dhanvantarinighantauh Edited by P.V. Sharma; Translated by Guru Prasad Sharma; Chaukhambha Orientalia, Varanasi Edn. 3rd, 2002 p. 81 Formulation ID: AK12/184 Formulation Name: Dadima GUna.
Mohammad Azam Khan; Muheet Azam vol. II (Part II) (19th century AD), Matba Nizami, Kanpur, 1898 AD p. 5-6 Formulation ID: AA26109 Formluation Name: Daaram/anar.
Mohammad Kabiruddin, Bayaaz-e-Kabir, vol. II (Compiled) Daftar-al-Maseeh, Karol Bagh New Delhi, 1938 AD p. 75 Formulation ID: MA3/232 Formulation Name: Rubb-e-Anaar Sheerin.
Mohammand Akbar Arzani: Qaraabaadeen Qaadri (17th centurty AD), Ahmadi Publication, Delhi, 1968 AD p. 213 Formulation ID: MH5/1476 Formulation Name: Safoof-e-Loolooee.
Sarngadharacarya; sarngadhara Samhita. Translated by Smt. Shailaja Srivastava: Chaukhamba Orientalia, Varanasi, Edn. 2nd, 1998 [Time of origin 13th century] p. 188 Formulation ID: AT/229. Formulation Name: Sunthyadicurna.

* cited by examiner

*Primary Examiner* — Susan Hoffman
(74) *Attorney, Agent, or Firm* — Peter B. Scull; Hamilton, DeSanctid & Cha, LLP

(57) ABSTRACT

A product of vegetal origin with a high percentage of proanthocyanidines with molecular weight of greater than 6000 daltons, a very high percentage of which proanthocyanidines have a molecular weight of greater than 30000 daltons, produces a great hypercholesterolaernic effect at acceptable doses for human consumption and little astringent and antinutritional effects. The product of vegetal origin may be presented as medicine, pharmaceutical composition, dietary complement or food product. An industrial process is provided for preparation of the product from dicotyledons.

21 Claims, No Drawings

PRODUCT OF VEGETAL ORIGIN COMPRISING PROANTHOCYANIDINES AND ITS PREPARATION PROCESS

CROSS-REFERENCE TO RELATED APPLICATIONS

The present application is the US national stage application of the Patent Cooperation Treaty (PCT) Application Number PCT/EP2005/052877, filed Jun. 21, 2005, entitled "PRODUCT OF VEGETAL ORIGIN COMPRISING PROANTHOCYANIDINES AND ITS PREPARATION PROCESS"; which designated all states including the United States of America; the subject matter of which hereby being specifically incorporated herein by reference for all that it discloses and teaches; and claims priority from the Spanish Patent Application, Number P200401626, filed Jun. 23, 2004, the subject matter of which also hereby being specifically incorporated herein by reference for all that it discloses and teaches.

This invention relates to the field of the pharmaceutical, dietary and food industries, in particular to products related to the control of risk factors of cardiovascular diseases.

BACKGROUND ART

A high level of cholesterol in the blood is a risk factor for cardiovascular disease. Different studies have demonstrated that people who consume diets rich in fiber have lower amounts of cholesterol and LDL in the blood than people who consume less fiber (cf. M. H. Davidson et al., "Effect of hydroxypropylmethylcellulose on serum lipids in subjects with mild-to-moderate primary hypercholesterolemia", *J. Am Col Card*, 1998, vol. 31(2) Suppl. A:319A). The beneficial effects of fiber are also known for protecting intestinal barrier integrity and preventing colon cancer.

Nevertheless, nowadays, the therapeutic application of dietary fiber supplements available in the market is very problematic, mainly due to the fact that these natural fibers are mixtures of substances with a highly variable and heterogeneous chemical composition, with the only common property that they are components of food that are not attacked by human digestive enzymes. Therefore, it is difficult to define the active ingredients in such supplements and to quantify the dosages.

Dietary fibers contain some pharmacologically active compounds, but they mainly contain products with little or no activity, such as celluloses or hemicelluloses. Minority components of the dietary fiber are polyphenols. The term polyphenol covers a large number of secondary metabolites of vegetables, which are structurally characterized by having aromatic rings with hydroxyl groups. In plants, polyphenols can be found free or associated to components of the cellular wall. This localization, together with their molecular weight, allows for differentiation between soluble and insoluble polyphenols. Insoluble polyphenols have a greater molecular weight and have the beneficial health effects indicated above.

Nevertheless, insoluble polyphenolic compounds are present in small amounts in fiber of the most commonly consumed vegetables or in commercial dietary supplements of fiber. Moreover, most of these insoluble polyphenols are not usable in their natural state in the necessary doses for chronic treatment of degenerative diseases, because they have a strong astringent and anti-nutritional effects due to the inhibition activity of the digestive enzymes, which form complexes with proteins.

One of the dietary fibers with higher polyphenol content is carob bean fiber, from the fruit of the carob tree (*Ceratonia Siliqua*). One commercial fiber with a high polyphenol content is called "carob fiber", of C.G.A. S.A. (cf. ES 2,060,543). Another carob bean fiber is described in the patent document ES 2,204,301. Both fibers have a polyphenol content of approximately 50% of the dry weight. These fibers reduce cholesterol levels in rats, but extrapolation to a human scale of the doses used in studies with animals would require amounts between 25 and 50 g/day, which are very high doses for therapeutic use.

Attempts have been made to increase the insoluble polyphenol content in dietary fiber. One example is a carob bean fiber containing nearly 90% of insoluble polyphenols that have been thermally modified in order to eliminate their astringent and anti-nutritional effects (cf. ES 2.187.356).

SUMMARY OF THE INVENTION

It is desirable to provide a dietary fiber with a high percentage of insoluble polyphenols with the aim of producing a maximum hypocholesterolaemic effect at acceptable doses for human consumption and with low astringent and antinutritional effects. It is also desirable to provide industrially viable processes for preparation of such dietary fiber.

Thus, discussed herein is a new product with a high percentage of polyphenols of high molecular weight. Also discussed are industrial processes for preparation of such a product.

In a first aspect the product of vegetal origin may comprises about 65-97% percent by weight of proanthocyanidines with a molecular weight greater than 6000 daltons, wherein more than about 50% percent by weight of said proanthocyanidines may have a molecular weight greater than 30000 daltons. In a particular embodiment of the product, the percent by weight of the proanthocyanidines with molecular weight greater than 6000 daltons may be about 90-97%. Particularly, the percent by weight of the proanthocyanidines with molecular weight greater than 30000 daltons versus the proanthocyanidines with molecular weight greater than 6000 daltons may be higher than about 60%.

Even though there are some distinctions, for the purposes of the descriptions herein, the term "proanthocyanidine" is considered to be a synonym of the term "condensed tannin", as both are chemically polymerized derivatives of flavonoids, mainly of flavan-3-ol. Thus, both are a type of high molecular weight polyphenol.

In another particular embodiment, with the intention of reducing possible astringent and anti-nutritional effects, the product of vegetal origin indicated above may further comprise about 0-2% percent by weight, and particularly about 0-1% by weight, of cold water-soluble polyphenols.

The composition of the product of vegetal origin, depending on the vegetal variety used and the specific conditions of the preparation process is as follows:

Humidity: about 0-10%
Minerals: about 2-10%
Proanthocyanidines with molecular weight greater than 6000 daltons: about 65-97% (proanthocyanidines with molecular weight greater than 30000 daltons: more than about 50% of said proanthocyanidines)
Water-soluble polyphenols: about 0-2%.
Celluloses and hemicelluloses: about 0-5%.
Lignin: about 0-10%
Oligosaccharides: about 0-5%
Proteins: about 0-5%

The product of vegetal origin of the present invention generally takes the form of a brown amorphous powder. It is not very soluble in water and in low molecular weight alcohols at room temperature. Its solubility rises when the temperature is close to the boiling point of the solvent or of the solvent mixture. These solutions give a positive reaction of polyphenols with Folin-Ciocalteau reactive and a precipitation with lead salts. The product of vegetal origin is a product mainly indigestible and non-absorbable in the mammalian or human intestinal tract.

Due to the chemical structure of the proanthocyanidines present in the product of the invention, the proanthocyanidines produce a hydrophobic-type interaction with cholesterol and bile salts, which are then eliminated through feces as complexes with said proanthocyanidines. Therefore, the enterohepatic cycle of cholesterol and bile salts is interrupted and thus, cholesterol diminishes in the organism. Due to the enrichment in proanthocyanidines with high molecular weight, the product of vegetal origin of the invention produces a maximum hipocholesterolaemic effect at acceptable doses for human consume, usable in a pharmaceutical form, and with low astringent and anti-nutritional effects.

In a particular embodiment of the invention, the product may be obtained from dicotyledons. It may be obtained from the whole plant or from parts of it, including fruits in a ripe state and preferably dried fruits. Plants and their fruits may be collected in a ripe state, generally at the end of summer, and may be left to dry in the shade at room temperature and at low relative humidity conditions. Examples of appropriate vegetal varieties that may be used for the preparation of the product of the invention are lucerne (*Medicago sativa*), field eryngo (*Eryngium campestre*), holm oak bark (*Quercus ilex*), pomegranate tree (*Punica granatum*) and quebracho (*Aspindosperma quebracho-bianco*). Examples of fruits that may be used are carob bean (*Ceratonia siliqua*), fruit from walnut tree (*Juglans regia*), olive (*Olea europea*), blueberry (*Vaccinuium myrtillus*), pomegranate (*Punica granatum*) and apple (*Pyrus malus*). Preferably, the product of the invention is obtained from pomegranate or from carob bean pulp.

In a second aspect, the preparation process of the product of vegetal origin described above may comprise the steps of: (a) performing a wash of the crushed vegetal material with a liquid selected from the group consisting of water between about room temperature and 60° C.; a mixture of water and a $C_1$-$C_3$ alcohol between about 20:80 and about 5:95 (v/v) at about room temperature; and a mixture of water and acetone between about 20:80 and about 40:60 (v/v) at about room temperature; and separating the solid and the liquid resulting from the wash, as many times as needed to get the washing liquid to remove less than 50 g of material per liter of washing liquid; (b) performing an extraction from the solid obtained in step (a) at about room or pressurized pressure, in conditions selected from the group consisting of water between about 80° C. and its boiling point; a $C_1$-$C_3$ alcohol between about 40° C. and its boiling point; a mixture of water and a glycol between about 80° C. and its boiling point; dimethylformamide between about 80° C. and its boiling point; and dimethylsulphoxide between about 80-150° C., and separating the solid and the liquid resulting from the extraction keeping a temperature higher than about 40° C.; (c) chilling the liquid obtained in step (b) and collecting the resulting precipitate, optionally evaporating part of the solvent before chilling; (d) drying the precipitate obtained in step (c) until the solvent content is lower than about 10% percent by weight; (e) subjecting the product obtained in step (d) to about 120-180° C. for at least 3 minutes; and (f) chilling the product obtained in step (e).

Preferably, the starting vegetal material for this process is a commercially dehydrated and crushed pulp. When carob bean is used, pulp without seeds would be preferable, but depending on the fruit or the vegetal variety, seeds could be included. Noncommercial vegetal material may have to be washed by water shower and be dried by an air flow before the extraction process. The dried vegetal material may then be crushed by a hammer mill until the size of the constituent particles is less than 3 cm in diameter.

The washing process of the crushed vegetal material may be performed in diffusion containers or in stirred tanks with water between about room temperature and 60° C. The ratio of vegetal material to water is between about 1:4 and 1:10 (w/w). As an alternative, the washing may be performed with a mixture of water and a $C_1$-$C_3$ alcohol between about 20:80 and 5:95 (v/v) at room temperature. The alcohol is preferably methanol or ethanol and more preferably methanol and the ratio of vegetal material to the mixture of water and methanol is about 1:4 (w/w). The washing may also be performed with a mixture of water and acetone between about 20:80 and about 40:60 (v/v) at about room temperature. In a particular embodiment, the ratio of water to acetone is about 30:70 (v/v) and the ratio of vegetal material to the mixture of water and acetone is between about 1:2 and 1:3 (w/w).

The solid and the liquid resulting from the wash may be separated by centrifugation, filtration or decantation, repeating the process from the resulting solid as many times as needed to get the washing liquid to remove less than about 50 g of material per liter of washing liquid, and preferably less than about 10 g of material per liter of washing liquid.

In case of vegetal products that are very rich in cellulose, it is advisable to use a previous operation of fermentation, in order to increase the yield of the extraction. The vegetal residue, from which water-soluble compounds have already been eliminated, may be submerged in a tank with water at a temperature of about 37° C. (between about 1 and about 3 kg of water per kg of wet residue). The residue may be added to this tank filled with water, the pH may be rebalanced to about 5 and an enzyme may be added, in particular beta-glucosidase (cellulase), between about 1 and about 25 g per kg of wet residue, depending on the desired magnitude of cellulose hydrolysis, and the mixture may be maintained and stirred at about 37° C. between about 2 and about 4 hours. At a later stage, the content of the hydrolysis bath may be decanted or centrifuged, and the supernatant with sugars from the hydrolysis of celluloses may be discarded and the residue may be washed with water at about 50° C. (about 4 kg of water per kg of wet residue), it may be centrifuged again and the supernatant may be discarded.

From the obtained solid at the washing step, whether using the intermediate fermentation process or not, an extraction may be performed in diffusing containers or in stirred tanks. The extraction may be performed with water between about 80° C. and its boiling point, at conditions of about room or pressurized pressure. The ratio of solid versus water may be between about 1:2 and about 1:3 (p/p). As an alternative, the extraction may be performed with a $C_1$-$C_3$ alcohol at a temperature between about 40° C. and its boiling point, preferably methanol between about 40° C. and its boiling point, and with a ratio of solid:methanol between about 1:4 and about 1:6 (p/p). The extraction may also be performed with a mixture of water and a glycol, preferably propylene glycol, at a temperature between about 80° C. and its boiling point. Finally, the extraction may also be performed with dimethylformamide between about 80° C. and its boiling point or dimethyl sulphoxide between about 80-150° C. In a particular embodiment of the invention, the extraction lasts from about 1 to about 4 hours, and more preferably between about 3 and about 4 hours. Solid and liquid resulting from the extraction are separated by any suitable method, as decantation, filtration or centrifugation, while keeping the temperature above about 40° C.

Next, the dark liquid obtained in the previous step may be chilled, usually in decantation tanks. The standing time can vary between about 4 and about 10 hours. During the process a dark brown precipitate may be formed that corresponds to the fraction of the target proanthocyanidines contained in the vegetal product. In the case that no precipitate is formed, it may be convenient to concentrate the obtained extract by solvent evaporation at low temperature with a reduced pressure at conditions of about 50 or about 60° C. and from about 0.8 to about 0.9 kg of absolute pressure. On the contrary, in case of using universal solvents as DMSO, DMF or glycols it may be convenient to dilute them with cold water or with an alcohol such as ethanol, propanol, iso-propanol or similar, which allows the precipitation of the low-solubility condensed proanthocyanidines. The resulting precipitate may be collected by common methods as decantation, filtration or centrifugation.

The precipitate obtained in the previous step is dried, preferably by hot air flow over plates until the solvent content is less than about 10% by weight. In a particular embodiment, the precipitate is dried at about 80-90° C. Next, the obtained product is subjected to temperatures of about 120-180° C. for at least for 3 minutes. Thus, by substantially eliminating the water from the precipitate, a controlled and homogeneous increase of the temperature of the product and a high polymerization at a very high temperature are achieved, without the risk of overheating that occurs at longer polymerization treatments with wet product. Thus, the polymerization rate is greater when compared with other types of denaturization treatments.

Finally the product is chilled. A final product may be obtained with a substantially vitreous aspect, and a brown color, and which is easily broken. Once cold, the product may be milled by hammer mills with a mesh sieve to 0.5 mm until getting a size less than about 180 µm. The product may be passed through a sieve with a mesh of about 180 µm and the brown colored product may be recovered.

By the procedure set forth above, between about 1 g and about 20 g of product of vegetal origin per kg of dry processed vegetal may be obtained, depending on the agronomic variety and on the conditions of the extraction.

In another aspect, the product of vegetal origin may provide a pharmaceutical composition comprising a therapeutically effective amount of the product of vegetal origin defined above, together with pharmaceutically acceptable excipients. The invention also may provide a dietary complement comprising an effective amount of the product of vegetal origin defined above, together with appropriate amounts of excipients. Moreover a food product may be provided, which comprises a nutraceutically effective amount of the product of vegetal origin as defined above, together with appropriate amounts of other edible ingredients.

The most common presentation forms for the pharmaceutical product and the dietary complement may be suspensions, capsules, tablets, powder or pellets; however, this listing does not exclude other forms that the person skilled in the art may consider viable for the administration of the product. The food product may be, but is not limited to, a form such as cookies or similar, or a spreadable cream form.

In another aspect, the product may be used for the preparation of a medicament, a pharmaceutical composition, a dietary complement or a food product for the treatment and/or the prevention of the hypercholesterolaemia and/or cardiovascular diseases in a mammal, including a human.

Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples are provided by way of illustration, and are not intended to be limiting of the present invention.

DETAILED DESCRIPTION OF PARTICULAR EMBODIMENTS

Preparation Process Starting with Pomegranate

This preparation process may be started with about 1000 kg of milled pulp of pomegranate fruit. The content in humidity should not be greater than about 10% (w/w) and the size should be less than about 3 cm. The milled pulp is treated with water at room temperature at about 1:10 ratio for approximately 4 hours. The washing water may be eliminated with the dissolved products passing it through an approximately 100 µm sieve and the entire solid may be collected and put together with the rest of the solids. The previous washing process may be repeated two more times in order to eliminate the water-soluble molecules. The temperature of the last wash is increased to about 60° C. for a better extraction of the remains of soluble products. It is advisable to be careful to collect all the solids that remain in the 100 µm sieve. The solid residue may be treated in a tank with reflux, with a mixture of propylene glycol and water in a proportion of about 75:25 (v/v) at about 95° C. for approximately 4 hours to dissolve the proanthocyanidines. The hot liquid (≥80° C.) is filtered or centrifuged to obtain a dark brown solution that contains the proanthocyanidines. It is concentrated under vacuum at a temperature near about 60° C. until water is eliminated. The obtained liquid is cooled to about room temperature (for a minimum of 24 hours). The brown precipitate may be recovered by centrifugation and a wet brown-colored paste may be obtained. The previous liquid residue may be diluted with cold water in a dilution of about 1 volume of liquid residue to 9 volumes of water. The residue may be left for approximately 24 hours and the formed solid recovered by centrifugation. This formed solid may be combined with the solid obtained in the previous step. The obtained creamy paste may be spread over plates forming layers not thicker than about 0.5 cm and left in a drying oven at low temperature, not greater than about 80-90° C., until the humidity is reduced to about 10%. The oven temperature may be increased to about 150° C. and maintained for about 15 min. The obtained product generally has a dark-brown vitreous appearance. The obtained product may then be milled to a particle size less than about 170 µm, and passed through a 100 µm sieve. The yield is about 1-4% from the milled pomegranate fruit.

Preparation Process Starting with Carob Bean

Another preparation process may be started with carob bean pulp, clean, dried and without seeds. An amount of about 100 kg of carob bean pulp may be crushed passing it once through a hammer mill until a size of less than about 3 cm in diameter. The crushed product may be placed in stirring tanks, in 400 kg of a mixture of water:methanol in a ratio of about 20:80 (v/v) at room temperature for approximately 2 hours. The washing liquid may be discarded, repeating the process several times to eliminate the product of at a rate of less than about 10 g per liter. Later, the solid phase may be separated by decantation. The diffusion treatment at about room temperature with a mixture of water:acetone in a ratio of about 30:70 (v/v) (about 2 kg of water per kg of wet residue) may repeated with the solid phase for approximately 3 hours. Later, the extraction liquid may be separated by filtration and discarded. The solvent may be evaporated from the residue in vacuum heaters, spreading the residue over plates with a thickness of between about 1 and 1.5 cm and heating at about 45° C. for about 5 hours. The obtained solid may be subjected to a stirred diffusion treatment with water (about 2 kg of water per kg of wet residue), at about 100° C. for approximately 3 hours. Later, the extracting liquid may be separated from the insoluble material by hot filtration and the solid residue may be discarded. This liquid may be cooled in decantation tanks to attain a temperature of between about 15 and 20° C., maintaining it in such conditions for approximately 6 hours. The precipitate may be collected by decantation or centrifugation. The collected amount varies between about 0.2 and 2 kg of dry weight depending on the condition of the fruit. The evaporation of the water from the residue may be performed by spreading the residue over plates with a product thickness between about 1 and 1.5 cm, and drying it in heater for approximately 12 hours at about 0.2 atmospheres of pressure and about 85° C., until the water contact drops below about 10%. Finally, when the water content of the residue drops below about 10%, the dried product may be subjected to a temperature of about 180° C. in an air flow for approximately 3 minutes, followed by chilling at room temperature. The product, when cooled, may be milled in hammer mills with a mesh of less then about 0.5 mm until the product particles are less than 180 μm in diameter. The product may be passed through a sieve with a net size of 180 μm and the finished product may be obtained.

Effect of the Product of Vegetal Origin in Cholesterolaemia

Influence over cholesterolaemia in rats was studied with three types of dietary fiber and the product of vegetal origin of the invention: microcrystalline cellulose (CEL) AVICEL®, carob fiber (CF) from C.G.A. S.A., modified polyphenols (MP) according to the patent document ES 2.187.356 and the product of vegetal origin (PVO) described herein. The fibers were included in four semi-synthetic isocaloric diets adjusted to the nutritional needs of the rats. The base-diet used was AIN 93-G #110113 Purified Diet (Dyets Inc., Pennsylvania), and the only variable was the type of food fiber, always in a proportion of 5% of the diet. "Wistar" male rats were used, from the Servicio de Animales del Centro Mixto Departamento de Nutrición y Bromatologia I and from Instituto de Nutrición CSIC-UCM (Facultad de Farmacia U.C.M.), selected from the same litter. 40 young rats were used to develop an experimental cholesterolaemia provoked by the consumption of cholesterol in the amounts of 8 g/kg of diet and bovine bile 2 g/kg of diet, both from Farmitalia-Carlo Erba, Madrid, together with their maintaining diet, for a period of fifteen days. During the experimental period, the animals were placed in individual metabolism cells. The metabolism cells were kept in a room at 22±2° C., with an automatic light-darkness control (12:12 hours) and constant air circulation.

Rats were divided into 4 groups of 10 hypercholesterolaemiac rats (serum cholesterol 250±37 mg/dl). Each group, otherwise kept in the same conditions, consumed the cholesterol-supplemented diet for 20 days more, but included in their diet one of each of the assayed fibers at the level of 5%. During the experimental period of 20 days, the animals were fed following the same protocol. The initial serum cholesterol was determined by extracting blood from the tail vein of the animal by puncture, after a vasodilatation in a bath at 37° C. Blood was collected in a capillary tube treated with heparin, and cholesterol was quantified immediately by an automatic analyzer. Cholesterol after the 20 days was determined in serum by cannulating the jugular vein, after anaesthetizing the animals.

It was found (cf. TABLE 1) that cellulose did not affect cholesterolaemia. but serum cholesterol continued to increase in the animals that had consumed the cellulose. On the contrary, in the animals that consumed the fibers, such fiber intake reduced cholesterol from the initial value. Nevertheless, PVO produced a superior reduction of the serum cholesterol values of the animals. Thus, insoluble polyphenols of PVO have a superior cholesterol reduction effect over the CF, and superior also to MP, a product which has the best effect in treating cholesterolaemia described so far in a food fiber (cf. L. Pérez-Olleros et al., *J Sci Food Agric* 1999, vol. 79, pp. 173-8; H. J. Zunft et al., *Adv Ther* 2001, vol. 18, pp. 230-6; B. Ruiz-Roso et al., *Schironia*, vol. 2, pp. 5-9). This effect seems to be produced by the complexing of biliary salts with the insoluble polyphenols, which results in interruption of the cholesterol enterohepatic cycle.

TABLE 1 shows the evolution of cholesterolaemia of rats with experimental hypercholesterolaemia that took diets including microcrystalline cellulose (CEL), carob fiber (CF), modified polyphenols (MP) and the product of vegetal origin of the invention (PVO).

|     | serum cholesterol (mg/dl) day 0 | serum cholesterol (mg/dl) day 20 |
| --- | --- | --- |
| PVO | 250 ± 37 | 125 ± 18$^{abc}$ |
| CEL | 250 ± 37 | 275 ± 25 |
| MP  | 250 ± 37 | 140 ± 10$^{ab}$ |
| CF  | 250 ± 37 | 180 ± 20$^{ab}$ |

An $^a$indicates significant difference (p < 0.05) from the CEL lot;
a $^b$indicates a significant difference (p < 0.05) from basal hypercholesterolaemia, and
a $^c$indicates a significant difference (p < 0.05) from the MP lot.

Comparative Study: Comparison of the Effects of the Product of the Present Invention Over Those Generated by a Product Obtained Following the Process of WO2004/014150A In order to carry out the assays described below two products of vegetal origin were used:

Product 1 corresponds to the product described herein. This product has been obtained following the process described above.

Product 2 corresponds to a product previously known in the art. This product was obtained following the process described in the PCT application number WO2004/014150A.

Study 1

The lipid-lowering effect of the product 2, which is rich in polyphenols (50%), was investigated in a noncomparative, open-label pilot study. Over 8 weeks, 47 volunteers with moderate hypercholesterolemia (total cholesterol 232-302 mg/dl) consumed 15 g of product 2 per day. After 4 weeks, reductions of 7% in mean total cholesterol were noted.

Study 2.

In this randomized, placebo-controlled, double blind human trial, 58 volunteers with elevated serum cholesterol levels (200-299 mg/dl) consumed 15 g of product 2 per day (treatment group) or 15 g placebo (placebo group). After 4 weeks, the consumption of 15 g per day of product 2 led to a reduction of total cholesterol of 9% compared to the placebo group.

Study 3.

The lipid-lowering effect of the product of vegetal origin described herein (product 1) with high percentage of proanthocyanidines (80%) was investigated in a noncomparative, open-label pilot study. Over 4 weeks, 45 volunteers with moderate hypercholesterolemia (total cholesterol 232-302 mg/dl) consumed 6 g of product 1 per day. After 4 weeks, reductions of 30% in mean total cholesterol were noted.

Study 4.

In this randomized, placebo-controlled, double blind human trial, 48 volunteers with elevated serum cholesterol levels (200-300 mg/dl) consumed 8 g of product 1 per day (treatment group) or 8 g placebo (placebo group). After 4 weeks, the consumption of 8 g per day of product 1 led to a reduction of total cholesterol of 23% compared to the placebo group.

The results obtained are summarized in Table 1:

TABLE 1

| Product | Adult volunteers (number) | Doses (g/day) | Treatment (days) | Placebo group | Reductions on mean total cholesterol (%) |
|---|---|---|---|---|---|
| Product 2 | 47 | 15 g | 28 | No | 7% |
| Product 2 | 58 | 15 g | 28 | Yes | 9% |
| Product 1 | 45 | 6 g | 28 | No | 30% |
| Product 1 | 60 | 8 g | 28 | Yes | 23% |

These studies show that product 1 has a more pronounced effect on serum cholesterol in humans than a carob pulp preparation obtained following the process described in WO2004/014150A (product 2). As illustrated in the results above, an effective amount of product 1 (about 50% lower than the amount of the product 2) achieves a reduction in the total cholesterol of more than two hundred fold better than the reduction achieved with product 2.

The invention claimed is:

1. A process for preparing a product of vegetal origin, comprising the steps of:
   (a) washing crushed vegetal material with a liquid selected from the group consisting of:
      water between about room temperature and about 60° C.;
      a mixture of water and a $C_1$-$C_3$ alcohol between about 20:80 and about 5:95 (v/v) at about room temperature; and
      a mixture of water and acetone between about 20:80 and about 40:60 (v/v) at about room temperature;
      and separating a solid and a liquid resulting from the wash as many times as needed to get the washing liquid to remove less than about 50 g of material per liter of washing liquid;
   (b) performing an extraction from the solid obtained in step (a) at room or pressurized pressure, in conditions selected from the group consisting of:
      water between about 80° C. and about its boiling point;
      a $C_1$—$CH_3$ alcohol between about 40° C. and about its boiling point;
      a mixture of water and a glycol between about 80° C. and about its boiling point;
      dimethylformamide between about 80° C. and about its boiling point; and
      dimethylsulphoxide between about 80 and about 150° C.;
      and separating the solid and the liquid resulting from the extraction while maintaining a temperature of equal to or higher than about 40° C.;
   (c) chilling the liquid obtained in step (b) and collecting a resulting precipitate, optionally evaporating part of the solvent before chilling;
   (d) drying the precipitate obtained in step (c) to obtain a dried product with a solvent content equal to or lower than about 10% percent by weight;
   (e) subjecting the dried product resulting from step (d) to a temperature in the range of about 120° C. and about 180° C. for at least 3 minutes; and
   (f) chilling the product obtained in step (e).

2. The process according to claim 1, wherein the selected liquid in step (a) is water between about room temperature and about 60° C. and the vegetal material ratio versus water is between about 1:4 and about 1:10 by weight.

3. The process according to claim 1, wherein the selected liquid in step (a) is a mixture of water and methanol between about 20:80 and about 5:95 by volume at about room temperature and the ratio of vegetal material to the mixture of water and methanol is about 1:4 by weight.

4. The process according to claim 1, wherein the selected liquid in step (a) is a mixture of water and acetone in a ratio of about 30:70 by volume at about room temperature and the ratio of vegetal material to the mixture of water and acetone is between about 1:2 and about 1:3 by weight.

5. The process according to claim 1, wherein the selected liquid in step (b) is water at a temperature of between about 80° C. and its boiling point and the ratio of solid obtained in step (a) versus the water added is between about 1:2 and 1:3 by weight.

6. The process according to claim 1, wherein the selected liquid in step (b) is methanol at a temperature of between about 40° C. and about its boiling point and the ratio of solid obtained in step (a) versus the liquid is between about 1:4 and about 1:6 by weight.

7. The process according to claim 1, wherein the extraction in step (b) lasts between about 1 to about 4 hours.

8. The process according to claim 1, wherein the precipitate in step (d) is dried at a temperature of between about 80 to about 90° C.

9. The process according to claim 1, wherein between step (a) and step (b) a fermentation of the material is performed.

10. A product of vegetal origin obtained by the process according to claim 1.

11. The product of vegetal origin according to claim 10, wherein the product of vegetal origin is obtained from dicotyledons.

12. The product of vegetal origin according to claim 10, wherein the product of vegetal origin is obtained from pomegranate tree fruit.

13. The product of vegetal origin according to claim 10, wherein the product of vegetal origin is obtained from carob bean pulp.

14. The product of vegetal origin as according to claim 10, combined in a therapeutically effective amount together with pharmaceutically acceptable excipients.

15. A dietary complement comprising the product of vegetal origin as defined in claim 10, together with appropriate amounts of excipients.

16. The product of vegetal origin as defined in claim 10, combined in a nutraceutically effective amount with appropriate amounts of other edible ingredients.

17. A method of treatment of hypercholesterolaemia and/or cardiovascular diseases in a mammal, including a human, which comprises administering to said mammal in need thereof a therapeutically effective amount of a product of vegetal origin as defined in claim 10.

18. The method according to claim 17, wherein the product of vegetal origin is administered in the form of a medicament.

19. The method according to claim 17, wherein the product of vegetal origin is administered in the form of a pharmaceutical composition.

20. The method according to claim 17, wherein the product of vegetal origin is administered in the form of a dietary complement.

21. The method according to claim 17, wherein the product of vegetal origin is administered in the form of a food product.

* * * * *